(12) United States Patent
Michelmann

(10) Patent No.: US 8,022,359 B2
(45) Date of Patent: Sep. 20, 2011

(54) MEASURING THE MOBILITY OF MASS SELECTED IONS

(75) Inventor: Karsten Michelmann, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 223 days.

(21) Appl. No.: 12/472,897

(22) Filed: May 27, 2009

(65) Prior Publication Data
US 2009/0294647 A1 Dec. 3, 2009

(30) Foreign Application Priority Data

May 30, 2008 (DE) .......................... 10 2008 025 972

(51) Int. Cl.
*B01D 59/44* (2006.01)
*H01J 49/34* (2006.01)
(52) U.S. Cl. ....................... 250/282; 250/287
(58) Field of Classification Search .................. 250/286, 250/287, 290
See application file for complete search history.

(56) References Cited

U.S. PATENT DOCUMENTS

| | | | |
|---|---|---|---|
| 4,633,083 A | | 12/1986 | Knorr et al. |
| 4,707,602 A | * | 11/1987 | Knorr ........................... 250/282 |
| 5,719,392 A | | 2/1998 | Franzen |
| 5,847,386 A | | 12/1998 | Thomson et al. |
| 6,580,068 B1 | * | 6/2003 | Tarver et al. .................. 250/286 |
| 6,586,727 B2 | * | 7/2003 | Bateman et al. .............. 250/282 |
| 6,744,043 B2 | | 6/2004 | Loboda |
| 2005/0092911 A1 | | 5/2005 | Hoyes |
| 2006/0024720 A1 | * | 2/2006 | McLean et al. .................... 435/6 |
| 2008/0185513 A1 | * | 8/2008 | Belov et al. .................... 250/288 |
| 2009/0236514 A1 | | 9/2009 | Renner |

OTHER PUBLICATIONS

Belov, et al., "Multiplexed Ion Mobility Spectrometry-Orthogonal Time-of-Flight Mass Spectrometry", Analytical Chemistry, vol. 79, No. 6, Mar. 15, 2007, pp. 2451-2462.
Knorr, et al., "Fourier Transform Ion Mobility Spectrometry", Analytical Chemistry, 57, 1985, pp. 402-406, American Chemical Society.

* cited by examiner

*Primary Examiner* — Jack Berman
*Assistant Examiner* — David E Smith
(74) *Attorney, Agent, or Firm* — Law Offices of Paul E. Kudirka

(57) ABSTRACT

In an ion mobility spectrometer (IMS) coupled to a mass spectrometer (MS), the ion current from a suitable ion source is modulated with an analog modulation having a smooth modulation function, whose instantaneous frequency varies with time over a wide frequency range. The modulated ion current is continuously fed through a mobility drift region into the mass spectrometer, where the temporally varying ion current profile of at least one ion species is measured. The mobility spectrum of the ion species is then generated by correlating its ion current time profile with the modulation function.

15 Claims, 3 Drawing Sheets

MEASURING THE MOBILITY OF MASS SELECTED IONS

BACKGROUND

The invention relates to methods for measuring the mobility of mass-selected ion species in an ion mobility spectrometer (IMS) coupled to a mass spectrometer (MS). Ion mobility spectrometers, including those connected to mass spectrometers, are usually operated by injecting very short ion current pulses. The ions are continuously generated in an ion source and then admitted into the drift region of the spectrometer by a gating grid over a short time span. The time spans for the transmission are usually between 100 and 300 microseconds; recording of the spectrum takes approx. 30 milliseconds. This method only uses a maximum of about one percent of the ions produced in the ion source. The low degree of ion utilization produces relatively poor signal-to-noise ratios in the mobility spectra obtained, for which reason attempts have repeatedly been made to improve the degree of ion utilization (ion efficiency). An increase from one percent to about 50 percent would, in theory, increase the signal-to-noise ratio, and thus the sensitivity of the method as well, by a factor of seven.

Bipolar grids are usually used as gating grids to generate the short ion current pulses. The ions transmitted by the grid are then pulled through a collision gas in a drift region by an axial electric field, their drift velocity being determined by their "mobility", which, as is well known, in turn depends on their charge, their mass, their collision cross-section, their ability to become polarized, and also their tendency to form complex ions with molecules from the collision gas.

"Ion species" here denotes ions of a substance in a given charge state. The term ion species, as used here, includes both monoisotopic ions and the ions of the isotope satellites, but not ions of the same substance in different charge states. The ion species can consist of molecular ions or pseudomolecular ions, dimer ions or multimer ions, and all types of fragment ions. Ion complexes that form all types of bonds with molecules or molecular fragments of other substances shall also be included. Pseudomolecular ions are protonated or deprotonated molecules whose mass deviates from that of the molecule because of the mass of the proton.

All ions with the same charge experience the same tractive force from the electric field, but this force manifests itself in different drift velocities through the collision gas for ions with different mobilities, i.e. different collision cross-sections and different masses. For lighter ions in the order of magnitude of the mass of the collision gas, it is mainly the "reduced mass" of the ions, with minor influence of their collision cross-section, which determines their mobility; for heavier ions from several hundred or thousand atomic mass units upwards it is the particular form of the molecules that is decisive, the collision cross-section being the significant factor in the mobility. The collision cross-section depends to a large extent on the folding state of the ion, but also on the number of atoms in the molecule, and thus implicitly on the mass. The implicit dependence is roughly proportional to the square of the third root of the mass. The mobilities of ions of the same charge but different isotopic composition differ only slightly and cannot be separated in current mobility spectrometers.

In the ion sources usually applied in IMS, several ion species are generally formed from the molecules of one substance, mostly differing by charge, although they can also be ions of dimers or complexes with water and collision gas. Every ion species has a characteristic mobility. At the end of the drift region, the incident ion current is usually measured at an ion detector, digitized and stored as a "mobility spectrum" in the form of a digitized sequence of measured values. An evaluation of this mobility spectrum provides information on the mobilities of the ions involved and thereby—in pure mobility spectrometers—information about the substances involved.

The switching operation of the bipolar grid serves as the start time for measuring the drift velocity of the different bunches of ions. As the ions drift, the diffusion of the ions in the forwards and backwards direction generates a diffusion profile for each bunch of ions with the same mobility. In sufficiently long drift regions, this produces ion signals with the familiar bell-shaped curves of the Gaussian distribution to a very good approximation. The drift velocity is determined from the measured drift time in the center of the bell-shaped curve and the known length of the drift region in the drift tube of the spectrometer.

As a rule, the width of the bell-shaped curve of the ion signals is predominantly determined by diffusion. This results in a diffusion-defined mobility resolution $R_d$, which is almost constant across the mobility spectrum and proportional to the root of the ion charge, the strength of the electric drawing field and the length of the drift region. A reasonably good mobility spectrometer has a mobility resolution of about $R_d=20$ for singly charged ions, and this can just about satisfactorily resolve two ion species whose mobility differs by 10 percent because their signals differ by two complete full widths at half-maximum. Good mobility spectrometers have mobility resolutions of $R_d=50$ to 80 and can separate ions with mobility differences of only four percent or less. Today's best mobility spectrometers, developed non-commercially in a specialized research institutes, have mobility resolutions of $R_d=150$, which is sufficient to recognize two ion species whose mobilities only differ by just one percent.

In the following, we will initially deal with the better ion efficiency in pure ion mobility spectrometers. These spectrometers are often miniaturized, with drift regions of ten centimeters at most, operated at atmospheric pressure, and usually used to measure pollutants in ambient air. The pollutants, more generally called "analyte substances" below, are usually ionized in ambient air drawn in at atmospheric pressure, namely by so-called "chemical ionization at atmospheric pressure" (APCI) in reactions with reactant ions by protonation or deprotonation, whereby dimeric ions and complexes with water and collision gas molecules are also formed in addition to monomeric pseudomolecular ions. The ratios of the individual ion species with respect to each other depend on the concentration of the analyte molecules in the collision gas.

Nitrogen or air is usually used as collision gas, in which evenly distributed traces of water vapor (usually in carefully controlled concentrations) are present. The reactant ions are usually generated by beta emitters, for example $^{63}$Ni, but corona discharges and other electron beam generators and UV lamps are also used for this purpose. The reactant ions are formed in a reaction chain, which starts with the production of primary nitrogen ions and finishes with a number of different water complex ions. These water complex ions bring about the actual chemical ionization of the analyte molecules.

As they drift through the collision gas of the drift region at atmospheric pressure, the ions continually experience a very quick succession of new attachments and losses of $H_2O$ water molecules and $N_2$ nitrogen molecules. Statistically averaged, an analyte ion, whether it be a monomer or a dimer, thus contains $a \times H_2O$ and $b \times N_2$, where a and b are generally average, non-integral fractions. These changes happen very quickly, and so the peaks of the mobility spectrum are hardly broadened. If the ions of such a peak are transferred from atmospheric pressure into a connected mass spectrometer, a momentary state is frozen, just like in a flash photograph, and the mass spectrum obtained contains the ions with various states of attachment, and thus very different masses, side by side.

The following section describes attempts to increase the degree of utilization of the ions. F. J. Knorr et al. (Anal. Chem. 1985, 57, 402; U.S. Pat. No. 4,633,083 A) have proposed a method which operates with an axial ion beam modulated by two control grids. The modulation function used is a square-wave function, i.e. an alternating complete closing and complete opening of the grid. This type of modulation will be called "binary". The first control grid is positioned directly behind the ion source, the second directly in front of the ion detector. Synchronous modulation of both grids generates an interference value for the ion beam at which some ion species can pass through while others are kept back by the interference of their drift time with the phases of the grid modulation frequency. If this modulation frequency is altered, an interference spectrum ("interferogram") can be recorded, which can be transformed by means of a Fourier transformation from the frequency domain of the interferogram into the time domain, and thus into a mobility spectrum. The method, called "Fourier Transform Ion Mobility Spectrometry" by its authors, provides a theoretical ion utilization ratio of 25 percent because the ion quantities are halved at each of the two grids. Expectations for this method, however, were not fulfilled as far as the increase in the signal-to-noise ratio is concerned, and the method has not yet gained acceptance. In order to produce clean interferograms with this method, the modulation frequency must practically not vary at all during the drift time of the ions from the first gating grid to the second gating grid or to the detector. This requires the modulation frequency to change slowly.

In the patent specification U.S. Pat. No. 5,719,392 (J. Franzen, 1995), the ion current of an ion mobility spectrometer is modulated in a binary fashion by the gating grid with a rectangular temporal Hadamard pattern, where both the pulse widths of the ion packages transmitted as well as their separations are statistically distributed. The ion utilization thus increases to 50 percent. The evaluation to obtain the mobility spectrum can be done either by using a cross-correlation of the detector current with the applied pattern, or by using Fourier or Hadamard transformations. Using the Fourier transformation even makes it possible to obtain an improved mobility resolution by a partial deconvolution with the apparatus function. It has become apparent, however, that this evaluation procedure using the Fourier transform does not operate stably for a noisy detector signal. The method has not yet been used.

In a very recent patent application DE 10 2008 015 000.2 (U. Renner), the ion current from the ion source is analog modulated by a steady modulation function, e.g. a sine function, with an instantaneous frequency which varies over a wide frequency range; and the resulting ion current signal at the detector is decoded again by an analysis of the correlation with the modulation function. This results in an exceptionally noise-free mobility spectrum with very good mobility resolution. The mobility spectrum has an almost unprecedented quality. The ion utilization is 50 percent. The modulation can be performed with the usual gating grids that are present in these spectrometers. The modulation function can preferably be a linear or nonlinear "chirp", as it is known from ion cyclotron resonance mass spectrometry. Even though the improvement to the signal-to-noise ratio does not quite match the theoretical expectations, the quality of the results and the stability of the method outclass all other attempts to obtain a mobility spectrum with high ion utilization.

The above-mentioned mobility spectrometers all operate at atmospheric pressure. There is now an almost universally accepted method of coupling them to mass spectrometers, which uses a different pressure range for the mobility drift region. A pressure range of about 500 pascals is used; the drift region is increased to a length of between 40 centimeters and two meters or more; and the electric field strength is increased to 2,000 volts per meter or more. In this pressure range, the drifting ions appear to form scarcely any complexes with other substances, so the mobilities of the ion species can be measured without any interference. However, in the long drift regions, the ions also diffuse in a radial direction over wide sections, which means that quite large diameters must be chosen for these drift regions. There is substantial patent literature for these applications, but they all operate in the conventional way with short, individual ion pulses which are introduced into the drift region. The duty cycle for the ions generated in the ion source here also amounts to only between 0.5 and 1 percent. The ion sources used are mainly electrospray ion sources (ESI). The mobility analyses are aimed mainly at peptides, proteins or other biopolymers in order to identify the folding structures of these biopolymers and determine the parallel existence of different folding structures for otherwise identical ions of an ion species.

Only the patent A. V. Loboda, U.S. Pat. No. 6,744,043 B2 (2004) will be mentioned here for these low-pressure methods with coupling to mass spectrometry because it offers an interesting axial focusing of the drifting ions in the drift region, albeit this has already been described and claimed in principle in the patent specification Thomson et al. U.S. Pat. No. 5,847,386 (1998). The Loboda patent specification proposes an RF ion guide with radial collision focusing for the drift region, the ion guide being constructed as an RF multipole rod system or as a ring system.

The publication of Mikhail E. Belov et al., Analytical Chemistry, Vol. 79, No. 6, Mar. 15, 2007, 2451 ("Multiplexed Ion Mobility Spectrometry Orthogonal Time-of-Flight Mass Spectrometry") is the first to couple a low-pressure ion mobility spectrometer with high ion utilization to a mass spectrometer. Here, ions are pulsed into the ion mobility drift region just as usual, but the short ion pulses of equal duration are repeated with high repetition rate at quasi-stochastic time intervals, which are relatively long compared to the pulse duration. The time intervals were selected according to simulation trials so that they were between at least ten times up to 70 times longer than the pulse duration. Since the pulse duration is relatively short compared to the time interval between pulses, this method does not have a high ion utilization by itself; this could, however, be achieved by collecting the ions in an ion storage device before they are pulsed into the mobility drift region and by using special measures to pulse them in with as few losses as possible. For a primary ion beam with constant ion current, the varying collecting times produced varying numbers of ions in the individual pulses, which had to be taken into account during the evaluation by a calibration curve. This makes an otherwise very interesting publication complicated and, particularly, means that the dynamic measuring range of the TOF-MS cannot be utilized fully because there is always a danger that the TOF ion detector will be oversaturated by pulses with too high an ion density. The overall ion utilization given in this publication was about 50 percent, although this can be increased in principle to over 90 percent. The theoretical increase of the ion currents in the ion pulses was up to 70 times the ion current from the ion source, and the measured increase was up to 50 times. The dynamic measuring range of present-day commercial mass spectrometers is adjusted to the maximum ion currents achievable with the ion sources used. Even if these ion currents are only achieved with optimum substance supply, for example in the maximum of substance peaks from liquid chromatographs, excessive increases of the ion current are disadvantageous because they can lead to an oversaturation of the ion detector.

Depending on the substance supply to the ion source, time-of-flight mass spectrometers with orthogonal ion injection (OTOF) often only detect a few tens or hundreds of ions in a single mass spectrum, which is recorded in about 100 microseconds, and so the signal noise in these individual spectra is extraordinarily high. Such individual mass spectra cannot be evaluated individually in practice. Only in rare cases are around a thousand ions recorded in an individual mass spectrum at maximum substance supply, which means the saturation limit of the ion detector is reached. Since such an OTOF in normal operation requires many thousands of ions for a mass spectrum which can be readily evaluated, regular practice is to add together at least around 200, usually even between 500 and 1,000 mass spectra, to form a sum mass spectrum which can be evaluated. In the publication of Belov et al., in order to retain the time resolution of about ten kilohertz for measurement of the individual mass spectra for the mobility determination, the ion mobility separation was repeated 1,000 times, and the corresponding individual mass spectra from the repeated measurements were added together. Since every ion mobility separation takes about 127 milliseconds, this took a total time of 127 seconds.

Mass spectrometers can only ever determine the ratio of the ion mass to the charge of the ion. In the following, the term "mass of an ion" or "ion mass" always refers to the ratio of the mass m to the number z of elementary charges on the ion, i.e. the mass-to-elementary charge ratio m/z. The quality of a mass spectrometer is essentially determined by the mass resolution in addition to other criteria. The mass resolution is defined as $R=m/\Delta m$, where R is the resolution, m the mass of an ion measured in units of the mass scale, and $\Delta m$ the full width of the mass signal at half maximum, measured in the same mass units.

SUMMARY

In accordance with the principles of the invention, the ion current from the ion source is modulated with a smooth analog modulation function with a finite modulation period and an instantaneous frequency which varies over a wide frequency range. The ions of the ion current are fed through a mobility drift region into a mass spectrometer and the temporally varying ion current profile of at least one ion species is measured with the mass spectrometer. The mobility spectrum of this ion species is obtained from the temporal ion current profile by correlating it with the analog modulation function. The analog modulation function stands in contrast to the binary modulation used hitherto; the base of the analog modulation function might be, for instance, a sine function; but with steadily varying frequency. Symmetric modulation in the range from zero to one hundred percent of the ion current results in an ion utilization of about 50 percent, without leading to excessive increases in the ion current supplied by the ion source, as in the publication by Belov et al.

The mass spectrometer here can be a single-channel mass filter, for example a quadrupole mass filter, which can be used to directly measure the temporal ion current profile of a selected ion species. If the mass filter can be switched cyclically so as to transmit different ion species in sequence, it is thus also possible to intermittently measure the ion current profiles of several ion species, although the maximum possible mobility resolution can then no longer be achieved. It has proved advantageous for the quality of the mobility spectrum to measure the ion current profile several times in mass filters, for example between ten and one hundred times, to add together the digitized ion current profiles to form a sum ion current profile and to determine the mobility spectrum from the sum ion current profile.

If the mass spectrometer has a high acquisition rate for individual mass spectra, which should be at least around one kilohertz or so, it can also acquire a complete measurement series of individual mass spectra, from which it is then easy to select and compile the ion current profiles for large numbers of ion species on the basis of their masses. A time-of-flight mass spectrometer with orthogonal ion injection (OTOF), for example, can be used for this purpose. Nowadays, these instruments can be operated at spectral acquisition rates up to ten kilohertz.

Since the individual mass spectra generally incorporate only a few ions and can only be evaluated individually in exceptional cases, the measurement series can be repeated using identical modulation periods and corresponding individual mass spectra from the individual measurement series can be added together to form sum mass spectra. The ion current profiles of the ion species are then selected from the series of sum mass spectra. This therefore results in the same number of sum mass spectra as there are individual mass spectra in a modulation period, thus maintaining a high mobility resolution.

If one forgoes mobility resolution, a series of a sufficiently large number of consecutively acquired individual spectra can also be added together in each case, thus reducing the total measuring time. A mixed operation involving the addition of several consecutively acquired individual mass spectra to form partial sum mass spectra and the addition of corresponding partial sum mass spectra from repeat measurements of the measurement series to form sum mass spectra is also possible.

For the evaluation, the ion current profiles of selected ion species are chosen according to their mass from the sequence of individual or sum mass spectra and arranged as a series of intensity values. The maximum intensity values of the ion current signals in the mass spectrum can be used for this; but it is also possible to integrate the ion current over the width of one ion current signal. The ion currents of their isotope satellites can especially be included. Since the ion current signals of all ion species must always occur in all mass spectra because of the steady, though modulated, ion current (unless they are momentarily taken down to zero by the modulation), the ion current profiles are always complete and steady if the influence of signal noise is neglected. A simple correlation analysis with the modulation function is then used to create a mobility spectrum for this ion species from the ion current profile of one ion species. The mobility value of this ion species can be determined from the mobility spectrum. If ion species occur with different folding states, and if these are resolved according to their mobility, several mobility signals appear in the mobility spectrum.

The modulation function can preferably be a linear or a nonlinear chirp. The modulation period can preferably be about 100 to 1,000 milliseconds long, in which 1,000 to 10,000 mass spectra are then measured each time at a spectral acquisition rate of ten kilohertz. In this case, a chirp can pass through the frequency range from zero to a maximum of five kilohertz, preferably to about three kilohertz.

It should be noted here that this method at no time involves separation of ions according to their mobility. A modulated, unseparated current of ions of all mobilities always flows through the drift region, and the modulated currents of ions of different mobilities pass each other, each with its own different drift velocity. The drift velocities and mobilities are only determined by the demodulation.

The gating grid of a commercial ion mobility spectrometer can be used for this type of analog modulation; it even causes fewer problems than binary modulation with fast switching on and off, which is required for a square-wave modulation.

DETAILED DESCRIPTION

While the invention has been shown and described with reference to a number of embodiments thereof, it will be recognized by those skilled in the art that various changes in form and detail may be made herein without departing from the spirit and scope of the invention as defined by the appended claims.

Figure 6:
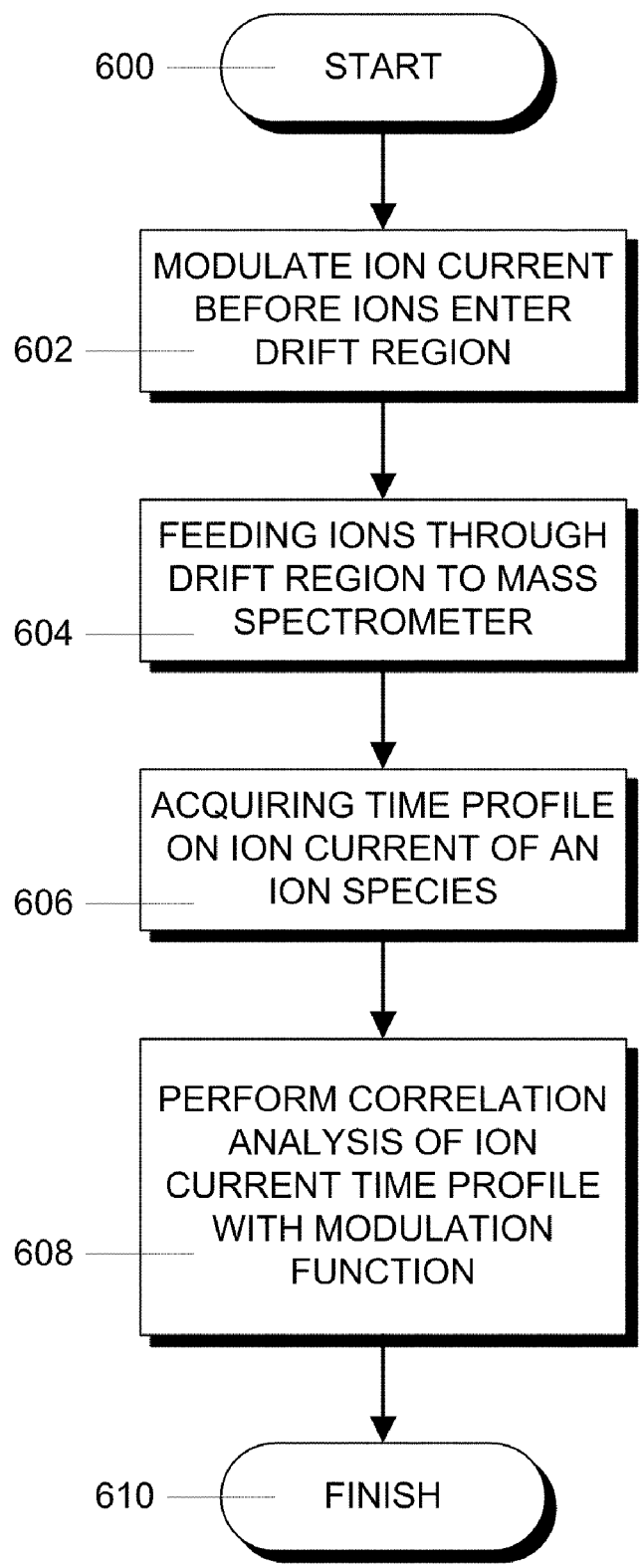
FIG. 6 is a flowchart showing the steps in an illustrative method for measuring the mobility of mass selected ions in accordance with the principles of the invention.

The steps in the inventive method are illustrated in FIG. 6. The method begins in step 600 and proceeds to step 602 where the ion current from the ion source is modulated with a steady modulation function having a finite modulation period and an instantaneous frequency which varies over a wide range of frequencies. In step 604, the ions of the modulated ion current are fed through a mobility drift region into a mass spectrometer. Next, in step 606, the temporally varying ion current profile of at least one ion species is measured with the mass spectrometer. Then, in step 608 the mobility spectrum of the one ion species is obtained from its temporally varying ion current profile by correlating it with the modulation function. The method then finishes in step 610.

The steady modulation function is smooth and continuous, does not contain any non-steady steps, in contrast to a binary modulation function, and is often called "analog modulation". As such a steady analog modulation function, for instance, a sine function can be used the frequency of which varies continuously. This results in an ion utilization of about 50 percent without leading to excessive increases in the ion current supplied by the ion source, as is the case in the method published by Belov et al. The dynamic measuring range of present-day commercial mass spectrometers is adjusted to the maximum ion currents of the ion sources used so that excessively increasing the ion current causes a detrimental oversaturation of the ion detector. This is avoided by the invention.

The basic principle of the method relies on the method in the above-cited patent application by U. Renner, which leads to outstandingly good mobility spectra for pure ion mobility spectrometers, but must be adapted to the requirements of the connected mass spectrometer. One problem which must be solved in particular is how to maintain the high measuring frequency that is required for a high mobility resolution. Renner used chirps extending from zero to seven kilohertz as modulation functions, and used a digitizing frequency of 40 kilohertz for the measurements of the modulated ion current at the detector of his mobility spectrometer.

Such a high digitizing frequency can just about be achieved when using a single-channel mass filter. The ions experience mixing of slower and faster ions as they pass through the mass filter and this limits the mobility resolution. However, as in the case of Renner, very good mobility spectra with resolutions of around $R_d=100$ are achievable when ions of a single mass are selected.

It is much more difficult to achieve such high mobility resolutions if series of complete or partial individual mass spectra are acquired, whether over broad or only limited mass ranges. An acquisition rate for mass spectra of 40 kilohertz is not yet possible today, even for very fast time-of-flight mass spectrometers with orthogonal ion injection. The maximum acquisition rate for the individual mass spectra here is currently only about ten kilohertz; and because the ions detected are usually only few in number, the individual mass spectrum obtained in this way can only be evaluated by itself in exceptional situations where substance supply and ion currents are optimally high. The conventional way of obtaining mass spectra that can be readily evaluated in such time-of-flight mass spectrometers without upstream drift regions consists in adding together a series of several hundred consecutively acquired individual mass spectra. When these mass spectrometers are coupled to mobility spectrometers, however, this method reduces the resolution for the mobility measurement so drastically that the method becomes useless.

The proposal according to the invention is thus that the measurement series for individual mass spectra are repeated with the same modulation periods; that the individual mass spectra which correspond with each other from the individual measurement series are added together, thus maintaining the mobility resolution of the individual mass spectra that is achievable in principle. At a spectrum acquisition rate of ten kilohertz, each sum mass spectrum thus obtained represents a time period of 100 microseconds. Although the mobility resolution is then not quite as good as that provided by Renner's method for pure mobility spectrometry, it nevertheless approaches that of good mobility spectrometers with mobility resolutions of about $R_d=80$ if sufficiently long drift regions with sufficiently high field intensities are used. Depending on the demands placed on the quality of the mobility spectra and their dynamic measuring range, it is possible to use between a few tens and a thousand measurement series by repeating the modulation periods if the ion current supplied by the ion source over this period remains constant and has the same composition. This produces 1,000 to 10,000 sum mass spectra for the correlation analysis.

The term "corresponding mass spectra" and "mass spectra which correspond with each other" shall here denote those mass spectra which have the same location in the time sequence of the mass spectra within the repeated measurement series.

Although the ion source must be supplied with a constant mixture of substances over a long time for this type of mobility measurement, this method can be applied in a large number of cases. An example is the investigation of possible folding structures of proteins that have been synthesized in different ways or under different conditions and are available in sufficient quantities. A further example is quality control during the manufacture of peptides, which must be checked for the simultaneous presence of different folding structures. Depending on the demands placed on the quality of the mobility spectra and their dynamic measuring range, the total measuring time is then between 100 and 10,000 seconds, i.e. between about 2 minutes and three hours.

If, on the other hand, this ion mobility/mass spectrometer is coupled to an instrument for separating substances, such as a liquid chromatograph, for example, this method can no longer be used because each of these substances is only available at the ion source for a few tens of seconds at most. In this case, however, there is often no need for a high mobility resolution. It is possible to add together partial series, each with a sufficient number of consecutively acquired individual mass spectra, within a measurement series to form sum mass spectra. In particular, it is possible to use a mixed operation, for example, in which ten consecutive individual mass spectra are added together to give partial sum mass spectra, and corresponding partial sum mass spectra, each from 20 repetition periods of the modulation function, are summed to give sum mass spectra, resulting in a total measuring time of four seconds for a modulation period of 200 milliseconds, which is usually easily compatible with separation methods that are not too fast. This results in 200 sum mass spectra for evaluation by correlation with the modulation function.

Modern time-of-flight mass spectrometers use so-called transient recorders, which have a digitizing rate of two gigahertz, to quickly digitize the individual mass spectra. Transient recorders with higher digitizing rates of eight or even ten gigahertz are being developed. The digitizing rate limits the acquisition rate for the individual mass spectra. In future it can be expected that higher acquisition frequencies for individual mass spectra (or at least for limited mass ranges of the individual mass spectra) can be achieved and thus also higher mobility resolutions.

It is preferable to vary the modulation frequency in the form of chirps, a chirp being conducted from a lower frequency limit of zero hertz up to an upper frequency limit and extended over the complete modulation period chosen. The upper frequency limit determines the maximum mobility resolution. An upper frequency limit of about three kilohertz results in mobility spectrum signal widths at half maximum height of about 300 microseconds. This still corresponds to a surprisingly good mobility resolution of between about $R_d=60$ and $R_d=80$. It is preferable to use a "linear chirp" with a frequency increase that is linear in time. The modulation control signal for the gating grid is generated in practice by a digital-to-analog conversion of previously calculated values of the modulation function, which are stored in a memory for this purpose. The acquisition rates for mass spectra in the mass spectrometer must be fast enough and should be at least three times the upper frequency limit of the modulation function.

If the analog modulation is symmetrical between zero and one hundred percent of the ion current, then on a statistical average, 50% of all ions are transmitted without any increase in the ion current from the ion source. The variation of the modulation frequency in the chirp preferably starts at zero hertz and extends to about three kilohertz for a time-of-flight mass spectrometer with ten kilohertz acquisition rate for the individual mass spectra. This modulation affects all ion species; the patterns applied to the individual ion species shift along each other as a result of the different drift velocities of the ions as they pass through the drift region of the mobility spectrometer, and this causes the mass spectra to exhibit a complicated pattern of overlapping.

For the evaluation, the ion current profiles of selected ion species with the same charge level are extracted from the sequence of individual or sum mass spectra on the basis of their charge-related mass m/z. It is advantageous to add the ion currents of all isotope satellites. Steady ion current profiles result in each case because all ion species are always present in all mass spectra on account of the steadily modulated total ion current. Only if the ion current is momentarily brought to zero by the modulation are the masses of these ion species missing from the mass spectrum, and then only if ions of the same ion species do not occur for a second or even a third time in the mobility spectrum with different mobility. A correlation analysis with the modulation function is used to compile a mobility spectrum for each of the ion species from these ion current profiles. The mobility of the ion species can be derived from the mobility spectrum. If ion species occur with ions in different folding states, and if these are resolved according to their mobility, several mobility signals appear in the mobility spectrum.

Ions of different charge levels have different mobilities because of their different charge. Analyzing ions of one charge level can lead to a confirmation of the results from other charge levels. If three folding structures with different mobilities have been found for singly charged ions, for example, then it can be expected that they will also be found for doubly and triply charged ions of the same physical mass. In exceptional cases, a further protonation can also lead to a change in the folding.

In general, the method is not carried out with high numbers of different substances. If five substances are simultaneously subjected to this type of mobility measurement, for example, this usually results in singly, doubly, and triply charged ions from each substance in an electrospray ion source. These 15 or so types of ion in total, each having the same charge level, are termed "ion species" here; the ion species thus each consist of the ions of one isotope group with the same charge. It has proved expedient to group together all the ion currents of all signals of one isotope group and to introduce them into a common ion current profile. The fifteen ion current profiles thus produce fifteen mobility spectra. Even for a simultaneous analysis of 20 substances only about 60 mobility spectra result.

A quite interesting special case with many routine applications consists in analyzing just one ion species for the presence of ions with different mobilities. In this case, the modulated ion current of this one ion species can be introduced into a single-channel mass spectrometer, for example a quadrupole mass filter, after the drift region. The mass filter has a transmission that is exactly set to this ion species including isotope satellite ions. The instrument then immediately produces the ion current profile at the ion detector and the mobility spectrum is obtained from the profile by correlation analysis. An instrument for this method thus only needs to consist of ion source, modulation grid, drift region, quadrupole filter and ion detector with corresponding housing, vacuum pumps and electronics. It can provide high mobility resolutions, as have been achieved by Renner for pure mobility spectrometers.

The well-known method of MRM (multiple reaction monitoring), in which the quadrupole filter can be quickly switched cyclically backwards and forwards between different masses, can then be used to extend this method to two (or more) ion species so that, for example, the singly, doubly and triply charged ions of the same substance can be analyzed in order to obtain confirmation measurements for the presence of several folding structures. However, this type of operation immediately reduces the resolution in the mobility spectrum because the switching speed is limited to a few hundred microseconds.

The mobility spectra obtained from the ion current profiles by the correlation analyses have a smooth characteristic with a very high mobility resolution that conventional pulse methods can only match with narrow pulse widths. However, the pulse method, which produces very strong noise on the signals of the mobility spectrum, particularly with narrow pulse widths, due to much lower ion utilization; this is not the case with the modulation method according to the invention. The ratio of signal to noise is improved by a factor of four to five at roughly the same mobility resolution; this also improves the detection sensitivity by a factor of four to five.

The quality and type of the mobility spectra make them very well suited to obtain absolute mobilities for a comparison with theoretically derived mobilities for different folding structures, particularly if helium is used as the drift gas, which simplifies the theoretical calculations.

The modulation function can preferably be a linear or nonlinear chirp. The modulation period can be between about 100 and 1,000 milliseconds long, during which time a measurement series with 1,000 to 10,000 mass spectra are then measured in each case. In this case, a chirp can pass through the frequency range from zero to a maximum of about five kilohertz, preferably to about three kilohertz.

This method does not show at any time a separation of ions according to their mobility. A modulated, unseparated current of ions of all mobilities always flows through the drift region, and the modulated currents of ions of different mobilities shift along each other at their different drift velocities. The drift velocities, and thus the mobilities, are only determined by the demodulation of the individual ion currents.

It should also be noted that this type of modulation is different from the modulation familiar from communication technologies, in which usually a high frequency carrier signal is amplitude, frequency or phase modulated by a modulating signal. The information is then contained in the amplitude changes, in the frequency changes or in the phase jumps. The ion current which is modulated here has neither phase nor frequency initially; only the modulation function which modulates the ion current between zero and full current has phases and frequencies. Here, the modulation function is a coding, which subsequently allows the partial ion currents, with ions of different mobility, contained in the ion current to be recognized by means of the modulation pattern.

This does not mean, however, that the modulation function itself could not have a frequency or phase modulation applied to it. The designation "steady modulation function with varying instantaneous frequency" should therefore not be interpreted too narrowly. All conceivable forms of modulation functions shall be included here, as long as the modulation function remains steady.

The different methods shall now be presented using the suitable embodiments of the instruments in each case. As has already been mentioned, an advantageous embodiment of the method according to the invention can already be carried out in a mobility spectrometer with a single-channel mass spectrometer, i.e. a mass filter, which measures the ion current profile of the ion species selected.

Figure 1:
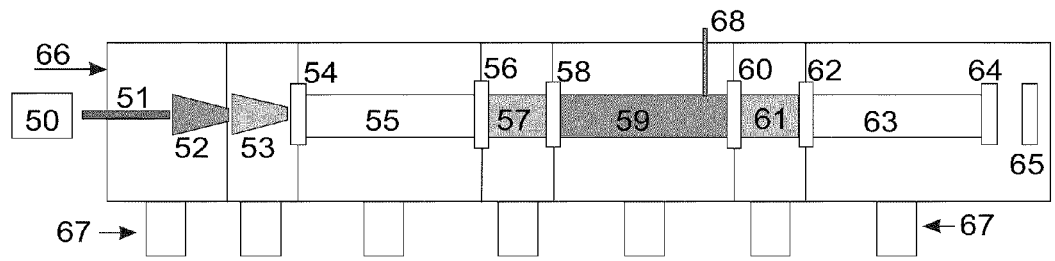
FIG. 1 is a schematic diagram of a mobility spectrometer that is coupled to a single-channel mass filter (63) at the end of the drift region (59). The ions produced in the electrospray ion source (50) are introduced via the inlet capillary (51) to a double funnel (52, 53), which feeds them via the modulation gating grid (54) to a first mass filter (55). The purpose of this additional, not absolutely necessary, mass filter (55) is to preselect one ion species in order to prevent a situation where an ion species with the same mass as the analyzed ions arises from other ion species by reactions or metastable decompositions and cannot be distinguished because of the moderate mass resolution in the mass filter (63). The selected ion species is introduced via ion lenses and pressure adjustment stages (56, 57, 58) into the drift region (59) and from there again via ion lenses and pressure adjustment stages (60, 61, 62) to the connected mass filter (63) with ion detector (65). The ion current profile of the selected ion species is measured in the ion detector (65), and correlation analysis is used to calculate the mobility spectrum from the ion current profile.
Figure 3:
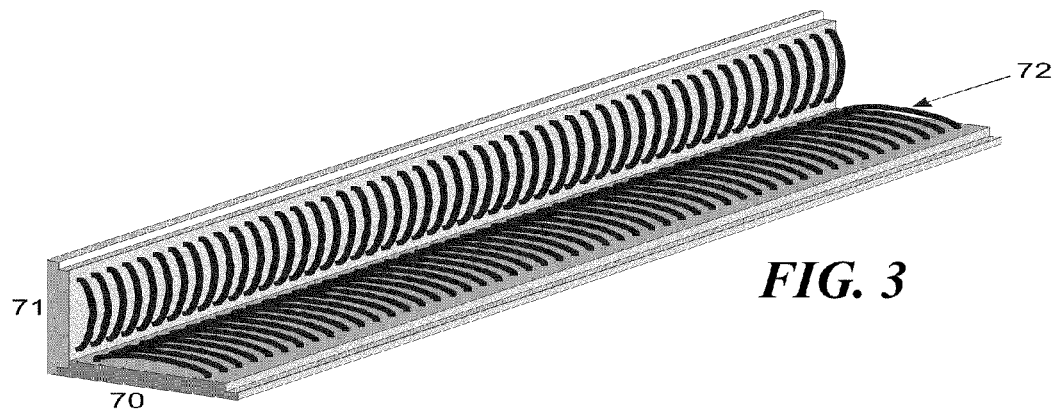
FIG. 3 shows an example of a drift region—a view into a quadrupole system for radial focusing which consists of a total of four ceramic plates, two of which are visible (70, 71), each with curved wires (72). The very precisely curved steel wires (72) are inserted into holes in the ceramic, held very accurately in position by a template and then secured with brazing solder. This arrangement can be used, on the one hand, to produce collisional focusing of the ions onto the central axis by means of a common RF voltage on all the wires of each pair of opposing ceramic plates, and, on the other hand, to generate an electric drawing field for the ions by means of uniformly distributed DC voltage differences between each pair of adjacent wires (72). The connections of the wires can be printed onto the rear of the ceramic plates (70, 71). Hexapole or octopole systems can be similarly constructed, generating a weaker axial focusing.

FIG. 1 shows the schematic diagram of such a mobility spectrometer, which is coupled to a single-channel mass filter (63) at the end of the drift region (59). The specific characteristic of the mobility spectrometer in FIG. 1 is that it has a further mass filter (55) to preselect the ion species in order to avoid overloading the drift region and, in particular, to avoid producing interfering reaction products from a large number of ion species. The ions generated in the electrospray ion source (50) are introduced via the inlet capillary (51) to a two-stage ion funnel (52, 53), which feeds them via the modulation gating grid (54) to the first mass filter (55). The selected ion species is introduced via ion lenses (56, 58) and pressure adjustment stage (57) into the drift region (59), supplied with gas via inlet (68), and from there again via ion lenses (60, 62) and pressure adjustment stage (61) to the connected mass filter (63) with ion detector (65). The pressure adjustment stages are always bridged by quadrupole ion guides (57, 61). The ion current profile of the ion species selected is measured in the ion detector (65), and the mobility spectrum is calculated by correlation analysis from the ion current profile. The drift region (59) here can be a collision-focusing quadrupole system, for example, as shown in FIG. 3.

The purpose of the additional, not absolutely necessary, mass filter (55) is to preselect one ion species in order to avoid a situation where an ion species with the same mass as the analyzed ions arises from a complex mixture of different ion species by reactions or metastable decompositions, and cannot be distinguished from the ion species under investigation because of the moderate mass resolution of the mass filter.

If both the mass filters (55) and (63) are operated in the MRM (multiple reaction monitoring) operating mode by switching to the transmission of different ion species, the mobility spectra of several ion species can be acquired simultaneously, although some mobility resolution is lost because there is a limit to the speed at which the switching operations can be carried out.

Figure 2:
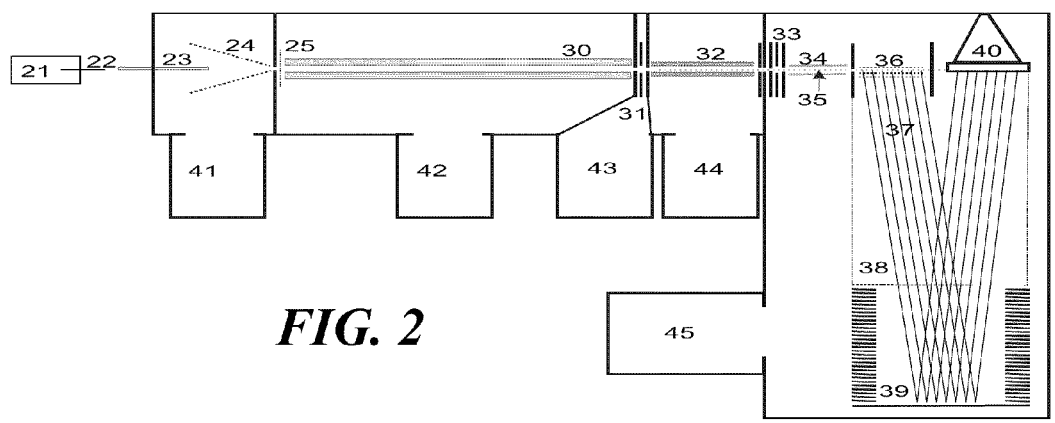
FIG. 2 shows a schematic array of an ion mobility spectrometer coupled to a high-resolution time-of-flight mass spectrometer with orthogonal ion injection. The analyte ions from the electrospray ion source (21, 22) are transported via an entrance capillary (23) into the vacuum system of the mobility spectrometer, where they are captured by an ion funnel (24) and introduced via the modulation gating grid (25) into the drift region (30). The drift region (30) here can take the form of a radially focusing quadrupole system, for example, as shown in FIG. 3. The ions are transmitted further via a pressure reducing stage (31) into another quadrupole ion guide (32), from where the ions are then injected into the pulser (36) of the time-of-flight mass analyzer (38) after being formed into a fine beam (35) by the lens system (33). Here they are pulsed out at right angles to their original direction of flight and form the beam (37), consisting of partial sections of the original ion beam. The ions of this beam (37) are reflected by a reflector (39) and impinge onto the detector (40) with high mass resolution. Vacuum pumps (41 to 45) maintain the vacuum in the various sections: a drift gas pressure of about 500 pascals is maintained in the drift region (30), a cooling gas pressure of about one tenth to one hundredth of a pascal in the quadrupole ion guide (32), and a residual pressure of about $10^{-7}$ pascals in the time-of-flight mass spectrometer.

If a relatively large number of mobility spectra are to be acquired for a mixture of substances, it is more advantageous to use a mass spectrometer which has a high acquisition rate for mass spectra, preferably higher than one kilohertz. FIG. 2 shows a schematic arrangement of an ion mobility spectrometer coupled to a high-resolution time-of-flight mass spectrometer with orthogonal ion injection. Mass spectrometers of this type can currently acquire mass spectra at a rate of ten kilohertz.

The analyte ions from the electrospray ion source (21, 22) are transported via an entrance capillary (23) into the vacuum system of the mobility spectrometer, where they are captured by an ion funnel (24) and introduced via the modulation gating grid (25) into the drift region (30). Here also, the drift region can take the form of a specially designed quadrupole system, as can be seen in FIG. 3. The ions are transmitted further via a pressure reducing stage (31) into another quadrupole ion guide (32), from where the ions are injected into the pulser (36) of the time-of-flight mass analyzer (38) after being formed into a fine beam (35) by the lens system (33). In pulser (36) they are pulsed out at right angles to their original direction of flight, and form the beam (37), which is reflected by a reflector (39) and impinges on the detector (40) with high mass resolution. Vacuum pumps (41 to 45) maintain the vacuum in the various sections: a drift gas pressure of about 500 pascals is maintained in the drift region (30), a cooling gas pressure of about one tenth to one hundredth of a pascal in the quadrupole ion guide (32), and a residual pressure of about $10^7$ pascals in the time-of-flight mass spectrometer (34-40).

Usually the drift region consists of a series of parallel electrode rings. Steadily increasing DC voltages at the electrode rings generate an electric drawing field along the axis, with electric fields strengths of between about 1,000 and 3,000 volts per meter. In these drift regions, the ions diffuse not only in the forwards and backwards direction but also in the radial direction, so the ions also spread out widely in the radial direction as they drift. They therefore have to be radially captured again, for which an additional ion funnel at the end of the drift region can be used, as described by Belov et al.

It is also possible to axially focus the ions during their drift, as proposed in the above-referenced Loboda patent for pulse-injected, mobility separated ion packets. FIG. 3 shows an example of such a radially focusing drift region—a view into a specially designed quadrupole system, which consists of a total of four ceramic plates, two of which are visible (70, 71), comprising curved wires (72). This arrangement can be used, on the one hand, to generate collisional focusing of the ions onto the central axis by means of a common RF voltage on the wires of each pair of opposing ceramic plates, and, on the other hand, to generate an electric drawing field for the ions by means of uniformly distributed DC voltage differences between each pair of adjacent wires (72). The collision focusing is brought about by the retroactive force of the pseudo-potential, in which the ions can oscillate radially, and by continuous damping of the kinetic energy and thus the oscillations of the ions.

One way of manufacturing this type of quadrupole system is to insert very precisely curved steel wires (72) into holes in the ceramic plates (70, 71); hold them very accurately in position by means of a template before securing them with brazing solder. It is thus possible to generate a quite precise electric field with good axial constancy in the interior. If the wires have a precise hyperbolic shape, a precise quadrupole RF field is generated in the radial direction. Such a quadrupole RF field is not necessarily required, however. Other shapes for the wires can therefore be more advantageous. The connections of the wires and some voltage supply circuits can be printed onto the rear of the ceramic plates (70, 71).

A similarly constructed hexapole or even an octopole system can be used instead of such a quadrupole system. These multipole systems focus less strongly; not forming the very thin, string-shaped ion current in the axis, which may cause problems with space charges. At the end of the drift region, a somewhat thicker string-shaped ion current can still be fed quite easily via pressure reducing stages to a quadrupole system with better focusing, which helps to form the fine ion beam for the pulser of the time-of-flight mass spectrometer. A favorable quadrupole ion guide provides a further axial electric field to guide the ions of the modulated ion beams quickly and without further diffusion towards the mass spectrometer.

The drift region contains a drift gas in a pressure range between about 100 and 1,000 pascals, preferably at a pressure of about 500 pascals. Helium is the ideal drift gas because it is then easier to make comparisons with theoretically derived mobilities of different folding structures, but it is also possible to use nitrogen, argon or another gas. The pressure in the drift region should be well regulated. In the low-pressure drift regions, stationary drift gas is normally used. In the Loboda patent, a counterflowing gas is used, which has an effect equivalent to lengthening the drift region for ion species of a particular mobility range. The flowing drift gas can only be used if the ions all drift in regions of the drift gas where the drift gas has the same velocity. For flowing gases in this pressure range, laminar flows with a parabolic velocity profile arise, which means this method can only be used with axial focusing of the ions.

Figure 4:
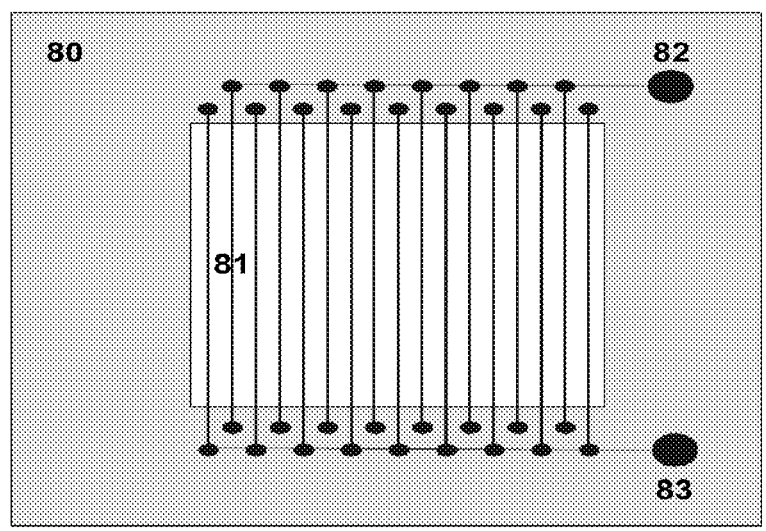
FIG. 4 shows a simple modulation gating grid constructed as a Bradbury-Nielsen grid with a bipolar arrangement of grid wires (81) with connections (82, 83) on a ceramic plate (80). Gating grids of this type are used in most mobility spectrometers.

The gating grids (54) or (25) in FIG. 1 or 2 can consist of very transparently arranged bipolar pole wires that are supplied, spatially alternating, with a different potential. Gating grids of this type are used in most mobility spectrometers; they are also surprisingly well suited for use as analog modulation gating grids. FIG. 4 shows such a modulation gating grid with a bipolar arrangement of grid wires (81) on a ceramic plate (80) with the two connections (82) and (83) for the two antipolar DC voltages, which cause the gate to close. When the gate is closed, the ions are fed to the wires, where they discharge. As the potential difference is increasingly removed, the grid is increasingly switched to transmission; the ions enter the next drift region and are pulled through the drift region by the electric field.

Figure 5:
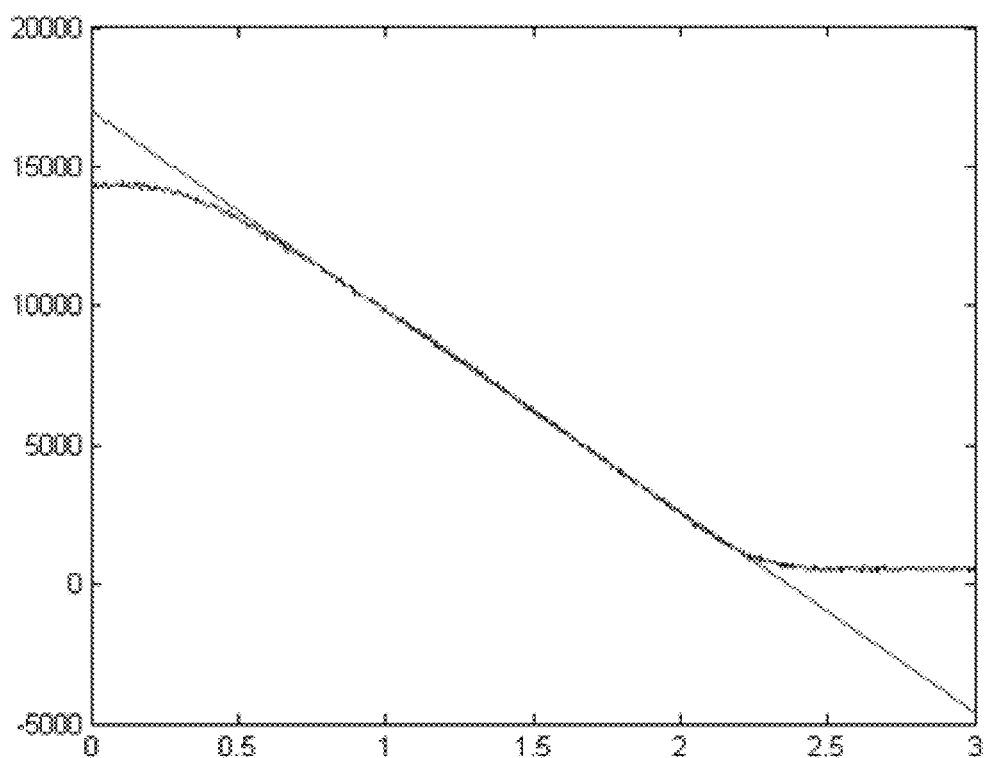
FIG. 5 represents the measured transmission curve of such a modulation gating grid for the ion current in picoamps (ordinate) as a function of the control voltage in volts (abscissa). The transmission curve (characteristic) has a broad linear operating range, which is very well suited for a modulation.

FIG. 5 shows the measured transmission curve of such a modulation gating grid for the ion current in picoamps (ordinate) as a function of the control voltage in volts (abscissa). The transmission curve (characteristic) has a broad linear operating range, which is eminently suitable for a modulation.

The development of such gating grids has so far been directed toward the generation of clean, short ion current pulses. There must be no overshooting of the blocking voltage, especially when the barrier potential is removed, because otherwise an unfavorable oscillatory structure would be imposed on the ion current pulses. Moreover, care has to be taken that the ions were able to pass through the grid as soon as the blocking voltage was removed. These characteristics are now beneficial to the analog control for the modulation.

The modulation with the steady analog modulation function with varying instantaneous frequency does not necessarily have to be performed by such a gating grid. The ion generation itself, for example, can be modulated, something which is possible with some types of ion generation such as photoionization. The transmission voltage for the ions into the ion funnels (24) or (52, 53) can also be controlled appropriately.

In order to perform a good correlation analysis of the ion current signal according to the invention, the modulation frequency has to be suitably varied following a time function. Chirps have proved to be particularly favorable for this. A chirp is a steady function with a phase function that varies quickly in time compared to the amplitude function. The modulation frequency changes monotonically from a lower frequency limit to an upper frequency limit. A linear chirp is a function where the frequency increases linearly with time. It is particularly favorable if the chirp is extended so that the modulation period chosen, for example one second, is completely filled.

Well-tried in practice for pure mobility spectrometers is a linear chirp whose lower frequency limit is zero hertz and upper frequency limit reaches about seven kilohertz. On the one hand, this upper frequency limit determines the maximum possible mobility resolution of the mobility spectrum obtained by the correlation while, on the other hand, it also has a smoothing effect on the mobility spectrum. As the mobility resolution is fundamentally limited by the diffusion broadening, the upper frequency limit of a preferred method is tuned to this mobility resolution. At the same time, all noise with a frequency above the upper frequency limit disappears from the mobility spectrum. To suppress so-called "side lobes", an amplitude modulation can additionally be imposed on the linear chirp or the frequency can be corrected in a nonlinear way.

The modulation frequency can, of course, also be modified toward lower frequencies by a reverse chirp. Other modification functions can also be used, including periodic functions or functions which are run through several times. It is also possible to use wavelets, for a fractal modulation, for example. However, periodic modification functions such as chirps, which are run through several times, entail the risk that artifacts which originate from ion current signals that are randomly periodically present may appear in the evaluated mobility spectrum. The simultaneous use of amplitude and phase modulation extends the possibilities of the modulation in a general way.

The analog modulation method described can be extended by using codes to change the phase function and the frequency in a continuous and a non-continuous way. In particular, pseudo-random codes, e.g. produced by Galois fields, can be used to bring about a phase change. Switching between the phases can be performed according to a coding, for example switching between two sinusoidal wave oscillations phase-shifted by 180°, favorably during zero crossover, which has been tried in practice for pure mobility spectrometers. Polyvalent codes, for example so-called Costas arrays, can be used for the frequency coding, where the frequency switchover occurs during zero crossover of a partial oscillation, so the modulation function remains steady.

The ion current profile of one ion species can be present as a temporally varying analog signal measured with the detector of a single-channel mass spectrometer, in real time or in an analog storage device; but usually it is present in a series of digital measurement values after digitization. These are stored in an electronic memory. The amplified ion current in real time or in the analog storage device shall be referred to here as the "analog ion current profile", and the digitally stored series of values as the "digital ion current profile".

The correlation of the ion current profile with the modulation function can be investigated either with the analog ion current profile, for example in an electronic correlator, or with the digital ion current profile by a suitable computer program. It is assumed here that the method of correlation is known, so it will not be described further. The result of correlating the ion current profile with the modulation function is then the mobility spectrum, which, in the first case, is obtained as an analog spectrum, and in the second case as a digital spectrum. To evaluate it further in a computer, the analog mobility spectrum must also be digitized.

Depending on the method, the mobility spectra obtained with this invention are moderately well to very well resolved and almost completely free of noise. Optimum methods improve the signal-to-noise ratio and thus the detection sensitivity by a factor of five compared to the simple pulse method. The mobility spectrum is exceptionally well suited to be fitted by Gaussian curves, even for small signals close to background. The correlation analysis operates very stably with this type of analog modulation, unlike with a square-wave modulation function.

The square-wave, i.e. binary, modulated ion currents with the two switching states "on" and "off", which have been applied almost exclusively up to now, are changed in an ion mobility spectrometer (in contrast to a time-of-flight mass spectrometer) by the diffusion processes during the drift in such a way that their evaluation, whether by correlation or by Fourier analysis, necessarily suffers from the mixture of binary switch coding and analog signal smearing brought about by the diffusion processes. This disadvantage of current methods is largely eliminated by this invention.

What is claimed is:

1. A method for measuring ion mobility spectra of selected ion species in an ion mobility spectrometer that is equipped with an ion source, an ion beam modulation device, an ion drift region and a mass spectrometer downstream of the ion drift region, comprising:
    (a) modulating the ion current from the ion source with a steady modulation function of finite modulation period before entering the ion drift region, the instantaneous frequency of the modulation frequency being continuously varied over a frequency range;
    (b) feeding ions of the modulated ion current through the ion drift region into the mass spectrometer;
    (c) acquiring with the mass spectrometer the time profile of the ion current of at least one ion species; and
    (d) performing a correlation analysis of the ion current time profile of an ion species with the modulation function to obtain the mobility spectrum of that ion species.

2. The method of claim 1, wherein the mass spectrometer comprises a mass filter and wherein step (c) comprises using the mass filter to transmit only the ion current of one single ion species and measure its ion current time profile.

3. The method of claim 1, wherein the mass spectrometer comprises a mass filter and wherein step (c) comprises switching the transmission of the mass filter cyclically between several ion species in order to measure the ion current time profiles of several ion species.

4. The method of claim 1, wherein the mass spectrometer can acquire mass spectra in a sequence of at least one kilohertz and wherein step (c) comprises acquiring a series of individual mass spectra with the mass spectrometer over the modulation period, and extracting ion current time profiles of ion species from the series of the individual mass spectra.

5. The method of claim 4, wherein the mass spectrometer is a time-of-flight mass spectrometer with orthogonal ion injection.

6. The method of claim 4, wherein step (c) comprises repeating the acquisition of the series of individual mass spectra using the same modulation period of the modulation function, adding together corresponding individual mass spectra of the acquired series along the modulation periods to form a series of sum mass spectra, and extracting the ion current time profiles of the ion species from the series of sum mass spectra.

7. The method of claim 6, wherein the mass spectrometer has an acquisition rate for mass spectra of at least five kilohertz, and step (c) comprises repeating the acquisition of the series of individual mass spectra between fifty and a thousand times.

8. The method of claim 1, wherein in step (a) the modulation function is a chirp.

9. The method of claim 8, wherein in step (a) the instantaneous frequency of the modulation extends from zero hertz to an upper frequency limit that is selected according to the resolution required.

10. The method of claim 9, wherein in step (a) the change in the modulation frequency spans the selected modulation period.

11. The method of claim 9, wherein the instantaneous frequency starts at zero hertz and increases linearly to the upper frequency limit.

12. The method of claim 9, wherein the instantaneous frequency is varied nonlinearly in the region between zero hertz and the upper frequency limit.

13. The method of claim 1, wherein, in step (a), the modulation is performed by a gating grid located at the beginning of the ion drift region.

14. The method of claim 1, wherein step (b) comprises axially focusing the ions by an RF multipole field as the ions drift through the drift region.

15. The method of claim 1, wherein step (b) further comprises axially focusing the ions by an RF field after the ions have drifted through the drift region.

* * * * *